United States Patent
Craig et al.

(10) Patent No.: US 7,904,154 B1
(45) Date of Patent: Mar. 8, 2011

(54) METHODS FOR MONITORING LAMINAR COORDINATION IN VENTRICULAR REPOLARIZATION AND FOR UTILIZING THE RESULTS OF SAID MONITORING IN CARDIAC DISEASE DIAGNOSIS AND TREATMENT

(76) Inventors: David Franklin Craig, Burnsville, NC (US); William David McGuinn, Jr., Columbia, MD (US)

( * ) Notice: Subject to any disclaimer, the term of this patent is extended or adjusted under 35 U.S.C. 154(b) by 1065 days.

(21) Appl. No.: 11/454,108

(22) Filed: Jun. 14, 2006

Related U.S. Application Data

(63) Continuation-in-part of application No. 10/241,857, filed on Sep. 13, 2002, now abandoned.

(51) Int. Cl.
  *A61B 5/02* (2006.01)
  *A61B 5/0452* (2006.01)
  *A61N 1/18* (2006.01)
(52) U.S. Cl. ............................................. 607/9; 600/508
(58) Field of Classification Search .................. 600/508; 607/9
See application file for complete search history.

(56) References Cited

U.S. PATENT DOCUMENTS

| | | | |
|---|---|---|---|
| 5,174,289 A | 12/1992 | Cohen | |
| 5,595,987 A | 1/1997 | Lasker et al. | |
| 5,840,762 A | 11/1998 | Bernstein et al. | |
| 6,167,412 A * | 12/2000 | Simons | 708/105 |
| 6,187,032 B1 * | 2/2001 | Ohyu et al. | 600/409 |
| 6,456,880 B1 | 9/2002 | Park et al. | |
| 6,915,156 B2 | 7/2005 | Christini et al. | |
| 6,963,907 B1 * | 11/2005 | McBride et al. | 709/219 |
| 2002/0138106 A1 | 9/2002 | Christini et al. | |
| 2004/0054380 A1 | 3/2004 | Craig et al. | |

* cited by examiner

*Primary Examiner* — Carl H. Layno
*Assistant Examiner* — Tammie K Heller
(74) *Attorney, Agent, or Firm* — Carter, Schnedler & Warnock, P.A.

(57) ABSTRACT

Methods for monitoring laminar coordination in ventricular repolarization and for utilizing the results of such monitoring in cardiac disease diagnosis and treatment. The methods include providing and administering a cardiac function test such as an EKG for examining human cardiac function. The cardiac function test in turn includes making a measurement of at least one marker. Healthy laminar coordination during repolarization is indicated by a measurement which meets an indicated threshold of measurement for the at least one marker. Malfunctioning laminar coordination is indicated by a measurement that does not meet the indicated threshold of measurement for the at least one marker. Malfunctioning laminar coordination is detected by locating a measurement that does not meet the indicated threshold of measurement for the at least one marker as an indication of malfunctioning laminar coordination within results of the cardiac function test. An electronic pacemaker may be employed as a treatment modality.

21 Claims, No Drawings

METHODS FOR MONITORING LAMINAR COORDINATION IN VENTRICULAR REPOLARIZATION AND FOR UTILIZING THE RESULTS OF SAID MONITORING IN CARDIAC DISEASE DIAGNOSIS AND TREATMENT

CROSS-REFERENCE TO RELATED APPLICATION APPLICATIONS

This is a continuation-in-part of and claims the priority benefit of U.S. patent application Ser. No. 10/241,857, filed Sep. 13, 2002, published as U.S. Patent Application Pub. No. US 2004/0054380 A1 on Mar. 18, 2004, titled "Enhancing Human Ventricular Contractility, Perfusion, and Rhythm by Enhancing Laminar Coordination of Ventricular Myocardial Repolarization by the His-Purkinje System," and now abandoned.

BACKGROUND OF THE INVENTION

This invention pertains to the practice of human medicine, and particularly to the management of diseases of the human heart. It pertains to using the principles of cardiac physiology and electrophysiology for the treatment of clinically demonstrable heart disease.

Each muscle cell, or myocyte, in the ventricles of the human heart is electrically active, maintaining a voltage across the enclosing cell membrane which at rest is negative on the inside surface relative to the outside surface, called the resting potential. Superimposed on this resting voltage can occur a time-limited swing in voltage called an action potential. The transmembrane voltage swings rapidly to a positive value, an event called depolarization. The voltage remains more positive than the resting potential for a period of time, and is said to be in the state of depolarization until it returns all the way to the resting potential. Repolarization is the event or process of returning to the resting potential. The period when the myocyte is depolarized is important in that contraction of the myocyte is occurring as long as the myocyte is depolarized, and because it is depolarized, due to release of calcium ions into the intracellular fluid.

In isolated or unregulated ventricular myocytes, the action potential duration (APD), the time from leaving the resting potential until reachieving the resting potential, ranges from about 200 to 300 milliseconds, averaging about 250 milliseconds. In the intact human heart under normal conditions, the outermost or subepicardial portion of the myocytes display this same APD. But the innermost or subendocardial portion of the myocytes display an APD of about 400 milliseconds during normal function. This local prolonging of APD in the subendocardial layer occurs due to regulation imposed from outside the myocytes by adjacent cells called Purkinje cells which comprise the Bundle Branches and the collected Bundle of His. The Purkinje cells have an APD averaging about 400 milliseconds, whether isolated or in the intact functioning heart. The Purkinje cells regulate the repolarization of the myocytes adjacent to them, delaying the myocyte repolarization until their own repolarization occurs. Since the Purkinje cells are most dense at the subendocardial surface of the ventricular wall, with a decreasing density as one looks outward through the wall, the subendocardial myocytes have a more prolonged APD than the subepicardial myocytes, but only when in an intact heart with fully functioning Purkinje cells and Bundle Branches. The Purkinje cell network has already been known to trigger the coordinated depolarization of myocytes, but its role in regulating repolarization to make a differential in the APD of myocytes according to layer has never before been recognized. This regulation of myocyte repolarization is a part of normal human physiology, and any weakening of it results in a disease state and a weakening of the primary function of the ventricles, which is to pump blood and maintain blood pressure.

The primary mechanism by which Purkinje cells regulate myocytes appears to be depletion of extracellular calcium ions in a restricted extracellular space around the myocytes. This lowered concentration facilitates outward calcium flow and inward sodium flow in the myocytes by the passive sodium-calcium exchange pump. This sustains a net inward current that prolongs the more positive electrical voltage that constitutes the depolarized state. The lowered extracellular calcium may also influence the gated ion channels that complete the repolarization process.

Delaying repolarization and prolonging the depolarized state in the subendocardial portions of the ventricular wall has at least the following beneficial effects at the more macroscopic level.

1) Contraction of the subendocardial layer continues longer than in the subepicardial layer.
2) Tissue pressure remains elevated longer into diastole (the resting phase between heart contractions) in the subendocardium, causing blood to flow into the capillaries in a wave after each contraction, which yields more efficient inflow of blood and oxygen into the subendocardial layer, and less acidosis.
3) The T wave generated by the noninvasive, body surface electrocardiogram (EKG) goes in the same upright direction as the dominant portion of the QRS complex, indicating healthy cardiac function, while without regulation of subendocardial APD the T wave deviates opposite the dominant portion of the QRS into a downward or inverted position.
4) The subendocardial myocytes adapt to optimize regulation by the Purkinje cells, allowing the Purkinje cells to suppress any dysfunctional electrical rhythms that arise from irritable foci in the ventricles or from circulating scroll waves introduced into the ventricles.
5) The Purkinje cells are relatively refractory to electrical stimulation backwards from the myocytes, due to their own optimization as a regulating organ, and thus are protected from serving as a channel for spread of ventricular arrhythmias. This refractoriness also makes the Purkinje cells available to suppress conduction of ventricular arrhythmias under normal pacemaking or artificially imposed overdrive pacing.
6) The contractility of the ventricle as a whole is sustained for a longer period when the Purkinje cells are successfully regulating subendocardial repolarization, yielding increased stroke volume, cardiac output, and energy efficiency.

All of these effects yield means of recognizing both healthy and impaired Purkinje function. When Purkinje function is impaired, disease states are caused that justify attempts to restore the normal physiology. These disease states can vary over the surface of a ventricle, for instance if only portions of the ventricles have impaired Purkinje function.

As used herein, the term "laminar coordination" is defined as the physiologic process by which each laminae, or layers, within the wall of a human heart ventricle undergo synchronized repolarization among themselves, while the sequence of spread of repolarization from one layer of myocardium to another is regulated by an external controller, the Purkinje fiber network of the His bundle and the bundle branches, and is not left to occur according to the intrinsic characteristics of the myocytes. In the normal state in the human, repolarization begins in the subepicardial layer, and then progresses through the more inward layers of myocardium, then last to the subendocardial layer. In the absence of imposition of regulation by the Purkinje cell network, the subendocardial layer would repolarize first, not last. This concept and process of laminar coordination of ventricular repolarization does not appear in any previous literature. The question of the mechanism by which repolarization is locally altered in the deep layers of the ventricles was formulated by Frank Wilson Md. in a 1931 paper, never answered adequately until now, and has not been addressed in the medical and physiology literature since 1957.

Previous mistaken attribution of regulation of ventricular repolarization to thermal gradients or ischemia has resulted in an inability to mitigate clinically the problems which result from defective regulation of ventricular repolarization, including heart failure, subendocardial ischemia, and ventricular arrhythmias.

SUMMARY OF THE INVENTION

In one aspect, a method for monitoring laminar coordination in ventricular repolarization is provided. The method includes providing a cardiac function test for examining human cardiac function, and administering the cardiac function test to a human. The cardiac function test in turn includes making a measurement of at least one marker. Healthy laminar coordination during repolarization is indicated by a measurement which meets an indicated threshold of measurement for the at least one marker. Malfunctioning laminar coordination is indicated by a measurement that does not meet the indicated threshold of measurement for the at least one marker. Malfunctioning laminar coordination is detected by locating a measurement that does not meet the indicated threshold of measurement for the at least one marker as an indication of malfunctioning laminar coordination within results of the cardiac function test.

In another aspect, a method for monitoring laminar coordination in ventricular repolarization, and for utilizing the results of the monitoring in cardiac disease treatment is provided. The method includes providing a cardiac function test for examining human cardiac function, and administering the cardiac function test to a human. The cardiac function test in turn includes making a measurement of at least one marker. Healthy laminar coordination during repolarization is indicated by a measurement which meets an indicated threshold of measurement for the at least one marker. Malfunctioning laminar coordination is indicated by a measurement that does not meet the indicated threshold of measurement for the at least one marker. Malfunctioning laminar coordination is detected by locating a measurement that does not meet the indicated threshold of measurement for the at least one marker as an indication of malfunctioning laminar coordination within results of the cardiac function test. A treatment modality to enhance laminar coordination is then provided and administered.

DETAILED DESCRIPTION OF THE INVENTION

In the human subject or patient, or in laboratory preparation, laminar coordination of ventricular repolarization may be monitored by one or more of the following markers, measured by providing and administering a cardiac function test to a human in a conventional manner:

1) the state of the T wave on the EKG reading;
2) the state of the T wave displayed from any leads present directly on the ventricular wall;
3) local myocardial cell action potentials displayed from any microelectrodes present;
4) local transmural pressure gradient cycles measured by microsensors which may be inserted in the ventricular wall; and/or
5) local cycles of concentrations of hydrogen, calcium, or other ions in the extracellular fluid of the ventricular wall as measured by any sensors or electrodes for the purpose that may be inserted in or placed upon the ventricular wall at any point of interest.

The electrodes used for electrical measurements during the cardiac function test, the sensors used for pressure and chemical measurements during the cardiac function test, and the recording, display, or analysis devices can be any commonly commercially available medical or laboratory components, as known by those of ordinary skill in the art.

Healthy laminar coordination during repolarization, whether initially present or present after successful treatment, is indicated by one or more of the following markers, while malfunctioning laminar coordination and, therefore, cardiac dysfunction, is indicated by measurements that do not meet the indicated thresholds for each marker, as follows:

1) upright, noninverted T waves in a reading from the EKG. The threshold of measurement is any net T wave voltage greater than zero. T wave width and T wave slope are not relevant to this evaluation.
2) upright, noninverted T waves from any electrodes in contact with the ventricular wall due to implantation or temporary placement during surgery. The threshold of measurement is any net T wave voltage greater than zero.
3) prolongation of subendocardial myocyte action potentials such that repolarization occurs after the termination of subepicardial action potentials. The threshold of measurement is termination of action potential voltage and return to baseline voltage in the subendocardial myocytes after the time of termination of action potential voltage of the subepicardial myocytes in the same patient or specimen at the same time under the same clinical or laboratory conditions.
4) instantaneous tissue pressure measurements in the subendocardium which exceed pressure measurements in the subepicardium at all time points from the beginning of the QRS complex on the EKG until the termination of the T wave on the EKG. The threshold of measurement is any pressure measurement in the subendocardial myocytes greater than the pressure in the subepicardial myocytes at any point in time within the above stated interval, in the same patient or specimen under the same clinical or laboratory conditions.
5) extracellular calcium concentrations in the subendocardium lower than in the subepicardium from the onset of QRS until the termination of the T wave. The threshold of measurement is any extracellular calcium concentration around the subendocardial myocytes instantaneously lower than the extracellular calcium concentration measured around the subepicardial myocytes in the same patient or specimen at the same time under the same clinical or laboratory conditions.
6) extracellular hydrogen ion concentrations in the subendocardium no higher than in the subepicardium at or just before the onset of QRS complexes. The threshold of measurement is any hydrogen ion concentration measured instantaneously around the subendocardial myocytes which is less than or equal to the concentration measured around the subepicardial myocytes at any point in time in the same patient or specimen under the same clinical or laboratory conditions. Accordingly, malfunctioning laminar coordination is detected by locating a measurement that does not meet the indicated threshold of measurement for the respective marker as an indication of malfunctioning laminar coordination within results of the cardiac function test.

The success of any treatment modality will be defined by the restoration of normal states of any markers as defined above in any regions which were not normal prior to treatment. Assessment of success or failure of any treatment modality may need to be prolonged for hours, days, or possibly weeks due to the "cardiac memory" effect of prolonged stress from prolonged states of absence of laminar coordination of repolarization. Absence of laminar coordination in any region of ventricular wall causes subendocardial ischemia which weakens Purkinje cell function locally and causes delay of return of full Purkinje cell control of repolarization until cellular healing occurs. Detriment to the patient by any prospective treatment modality will be defined by abnormality of any available markers post-treatment which were normal pre-treatment.

The least expensive and least invasive marker in routine clinical treatment will be the body surface electrocardiogram. This may also be used for followup monitoring as a proxy for other markers measured by more invasive means during treatment procedures or in the laboratory. Conventional existing electrocardiographic equipment could be used with the interpretation performed only by the human operator. A device may also be preprogrammed to automatically perform the analysis described above.

The enhancement or detriment of laminar coordination of repolarization when caused by any treatment modality or disease may be measured in a variety of ways. The initial best treatment modality to test is applying electronic pacemakers and leads to the portions of either or both human ventricles which are to have their regulating portion of the His-Purkinje system enhanced by triggering locally the electrical depolarization of the Purkinje cells by proper placement of electrodes as guided by the analysis of measurements as described above. Prospective drugs or other therapies which may regulate or enhance the cellular or subcellular structures and processes in Purkinje cells or ventricular myocardial cells by which laminar coordination is produced can also be assessed for efficacy.

Methods for monitoring laminar coordination in ventricular repolarization and for utilizing the results of such monitoring in cardiac disease diagnosis and treatment are described herein. Various details of the invention may be changed without departing from its scope. Furthermore, the foregoing description of the invention is provided for the purpose of illustration only and not for the purpose of limitation—the invention being defined by the claims.

What is claimed is:

1. A method for monitoring laminar coordination in ventricular repolarization, comprising:
providing a cardiac function test for examining human cardiac function, the cardiac function test including making a measurement of at least one marker, healthy laminar coordination during repolarization being indicated by a measurement which meets an indicated threshold of measurement for the at least one marker, and malfunctioning laminar coordination being indicated by a measurement that does not meet the indicated threshold of measurement for the at least one marker;
administering the cardiac function test to a human; and
detecting malfunctioning laminar coordination by locating a measurement that does not meet the indicated threshold of measurement for the at least one marker as an indication of malfunctioning laminar coordination within results of the cardiac function test.

2. A method according to claim 1, wherein the cardiac function test is an electrocardiogram reading, and the indication of malfunctioning laminar coordination is at least one inverted T wave shown on the electrocardiogram reading.

3. A method according to claim 1, wherein the cardiac function test is a reading from at least one electrode implanted or temporarily placed in contact with a ventricular wall, and the indication of malfunctioning laminar coordination is any net T wave voltage less than zero.

4. A method according to claim 1, wherein the cardiac function test is a comparison of a measurement of subendocardial action potential timing with a measurement of subepicardial action potential timing, and the indication of malfunctioning laminar coordination is termination of the subendocardial action potential occurring before termination of the subepicardial action potential.

5. A method according to claim 1, wherein the cardiac function test is a comparison of a measurement of subepicardial tissue pressure with a measurement of subendocardial tissue pressure, and the indication of malfunctioning laminar coordination is a subendocardial tissue pressure measurement less than a coincident subepicardial tissue pressure measurement at any time from the beginning of the QRS complex as shown on an electrocardiogram reading until termination of the T wave on the electrocardiogram reading.

6. A method according to claim 1, wherein the cardiac function test is a comparison of a measurement of extracellular calcium concentration in the subendocardium with a measurement of extracellular calcium concentration in the subepicardium, and the indication of malfunctioning laminar coordination is an extracellular subendocardial calcium concentration measurement greater than a coincident extracellular subepicardial calcium concentration measurement at any time from the beginning of the QRS complex as shown on an electrocardiogram reading until termination of the T wave on the electrocardiogram reading.

7. A method according to claim 1, wherein the cardiac function test is a comparison of a measurement of extracellular hydrogen ion concentration in the subendocardium with a measurement of extracellular hydrogen ion concentration in the subepicardium, and the indication of malfunctioning laminar coordination is an extracellular subendocardial hydrogen ion concentration measurement greater than a coincident extracellular subepicardial hydrogen ion concentration measurement at or just before the onset of a QRS complex shown on an electrocardiogram reading.

8. A method for monitoring laminar coordination in ventricular repolarization, and for utilizing the results of said monitoring in cardiac disease treatment, comprising:
providing a cardiac function test for examining human cardiac function, the cardiac function test including making a measurement of at least one marker, healthy laminar coordination during repolarization being indicated by a measurement which meets an indicated threshold of measurement for the at least one marker, and malfunctioning laminar coordination being indicated by a measurement that does not meet the indicated threshold of measurement for the at least one marker;
administering the cardiac function test to a human;
detecting malfunctioning laminar coordination by locating a measurement that does not meet the indicated threshold of measurement for the at least one marker as an indication of malfunctioning laminar coordination within results of the cardiac function test;

providing a treatment modality to enhance laminar coordination; and administering the treatment modality.

9. A method according to claim 8, wherein the cardiac function test is an electrocardiogram reading, and the indication of malfunctioning laminar coordination is at least one inverted T wave shown on the electrocardiogram reading.

10. A method according to claim 8, wherein the cardiac function test is a reading from at least one electrode implanted or temporarily placed in contact with a ventricular wall, and the indication of malfunctioning laminar coordination is any net T wave voltage less than zero.

11. A method according to claim 8, wherein the cardiac function test is a comparison of a measurement of subendocardial action potential timing with a measurement of subepicardial action potential timing, and the indication of malfunctioning laminar coordination is termination of the subendocardial action potential occurring before termination of the subepicardial action potential.

12. A method according to claim 8, wherein the cardiac function test is a comparison of a measurement of subepicardial tissue pressure with a measurement of subendocardial tissue pressure, and the indication of malfunctioning laminar coordination is a subendocardial tissue pressure measurement less than a coincident subepicardial tissue pressure measurement at any time from the beginning of the QRS complex as shown on an electrocardiogram reading until termination of the T wave on the electrocardiogram reading.

13. A method according to claim 8, wherein the cardiac function test is a comparison of a measurement of extracellular calcium concentration in the subendocardium with a measurement of extracellular calcium concentration in the subepicardium, and the indication of malfunctioning laminar coordination is an extracellular subendocardial calcium concentration measurement greater than a coincident extracellular subepicardial calcium concentration measurement at any time from the beginning of the QRS complex as shown on an electrocardiogram reading until termination of the T wave on the electrocardiogram reading.

14. A method according to claim 8, wherein the cardiac function test is a comparison of a measurement of extracellular hydrogen ion concentration in the subendocardium with a measurement of extracellular hydrogen ion concentration in the subepicardium, and the indication of malfunctioning laminar coordination is an extracellular subendocardial hydrogen ion concentration measurement greater than a coincident extracellular subepicardial hydrogen ion concentration measurement at or just before the onset of a QRS complex shown on an electrocardiogram reading.

15. A method according to claim 8, further comprising:
re-administering the cardiac function test to the human;
examining results of the re-administered cardiac function test for the indication of malfunctioning laminar coordination in order to determine the efficacy of the treatment modality.

16. A method according to claim 15, wherein the cardiac function test is an electrocardiogram reading, and the indication of malfunctioning laminar coordination is at least one inverted T wave shown on the electrocardiogram reading.

17. A method according to claim 15, wherein the cardiac function test is a reading from at least one electrode implanted or temporarily placed in contact with a ventricular wall, and the indication of malfunctioning laminar coordination is any net T wave voltage less than zero.

18. A method according to claim 15, wherein the cardiac function test is a comparison of a measurement of subendocardial action potential timing with a measurement of subepicardial action potential timing, and the indication of malfunctioning laminar coordination is termination of the subendocardial action potential occurring before termination of the subepicardial action potential.

19. A method according to claim 15, wherein the cardiac function test is a comparison of a measurement of subepicardial tissue pressure with a measurement of subendocardial tissue pressure, and the indication of malfunctioning laminar coordination is a subendocardial tissue pressure measurement less than a coincident subepicardial tissue pressure measurement at any time from the beginning of the QRS complex as shown on an electrocardiogram reading until termination of the T wave on the electrocardiogram reading.

20. A method according to claim 15, wherein the cardiac function test is a comparison of a measurement of extracellular calcium concentration in the subendocardium with a measurement of extracellular calcium concentration in the subepicardium, and the indication of malfunctioning laminar coordination is an extracellular subendocardial calcium concentration measurement greater than a coincident extracellular subepicardial calcium concentration measurement at any time from the beginning of the QRS complex as shown on an electrocardiogram reading until termination of the T wave on the electrocardiogram reading.

21. A method according to claim 15, wherein the cardiac function test is a comparison of a measurement of extracellular hydrogen ion concentration in the subendocardium with a measurement of extracellular hydrogen ion concentration in the subepicardium, and the indication of malfunctioning laminar coordination is an extracellular subendocardial hydrogen ion concentration measurement greater than a coincident extracellular subepicardial hydrogen ion concentration measurement at or just before the onset of a QRS complex shown on an electrocardiogram reading.

\* \* \* \* \*